(12) United States Patent
Oda et al.

(10) Patent No.: US 6,461,827 B1
(45) Date of Patent: Oct. 8, 2002

(54) METHODS AND KITS FOR DETECTING OR PREDICTING ISCHEMIC DISORDERS

(75) Inventors: Hiroshi Oda, Tsukuba (JP); Nobuyuki Sato, Tsukuba (JP); Masazumi Nishikawa, Tsukuba (JP); Kosuke Seiki, Tsukuba (JP); Yoshihiro Urade, Kyoto (JP); Yutaka Eguchi, Kusatsu (JP); Naomi Eguchi, Osaka (JP)

(73) Assignees: Mauha Corporation, Tokyo (JP); Osaka Bioscience Institute, Tokyo (JP)

( * ) Notice: Subject to any disclaimer, the term of this patent is extended or adjusted under 35 U.S.C. 154(b) by 0 days.

(21) Appl. No.: 09/423,104

(22) PCT Filed: Apr. 30, 1998

(86) PCT No.: PCT/JP98/01972

§ 371 (c)(1),
(2), (4) Date: Oct. 29, 1999

(87) PCT Pub. No.: WO98/49559

PCT Pub. Date: Nov. 5, 1998

(30) Foreign Application Priority Data

Apr. 30, 1997 (JP) .............................. 9/113126

(51) Int. Cl.⁷ .............................. G01N 33/53
(52) U.S. Cl. .................. 435/7.92; 435/7.1; 435/7.9; 435/7.91; 435/7.94; 435/810; 435/975; 436/63; 436/518; 436/805; 436/811
(58) Field of Search .................. 435/7.1, 7.92, 435/7.94, 283.1, 7.9, 7.91, 810, 975; 436/63, 811, 518, 805; 424/130.1

(56) References Cited

U.S. PATENT DOCUMENTS 4,503,143 A * 3/1985 Gerber ........................ 435/7
4,656,253 A * 4/1987 Lewicki ...................... 530/387
6,224,584 B1 5/2001 March et al.

OTHER PUBLICATIONS

Melegos et al Clinical Chemistry 42:12 1996.*
Hiraoka et al International Colloquium on Beta Trace.*
Oda et al Proc. Japan acad., 72 ser. B 1996.*
Hiraoka et al Biol. Pharm Bull. 16 (10) 949–(1993).*
Eguchi et al., "Expression of lipocalin–type prostglandin D synthase (Beta–trace) in human heart and its accumulation in the coronary circulation of angina patients", Proc. Natl. Acad. Sci. USA, vol. 94, pp. 14689–14694, Dec. 1997.
Tachibana et al., "Brain–type prostaglandin D synthetase occurs in the rat cochlea", Proc. Natl. Acad. Sci. USA, vol. 84, 7677–7680, Nov. 1987.
Nishigakada, Shinya, "Urinary excretion of human prostaglandin D synthase during various pathological states", Chemical Abstracts Service, Columbus, Ohio, Database Accession No. 1998:767753 XP002180935 (Abstract Only).
Watanabe et al., "Identification of beta–trace as prostaglandin D synthase", Biochemical and Biophysical Research Communications, vol. 203, No. 2, 1994, pp. 1110–1116.

* cited by examiner

Primary Examiner—Christopher L. Chin
(74) Attorney, Agent, or Firm—Fish & Richardson P.C.

(57) ABSTRACT

The present invention provides a method for detecting or predicting ischemic disorders in a subject by using as an indication the concentration of human lipocalin-type prostaglandin D synthase (hPGDS) in body fluid samples from the subject. More specifically, the method comprises comparing the hPGDS concentrations in the body fluid samples from a subject with the reference values established for a normal subject, thereby detecting or predicting the ischemic disorders.

41 Claims, 5 Drawing Sheets

COMPARISON OF hPGDS CONCENTRATION IN GREAT CARDIAC VEIN BLOOD BETWEEN NORMAL SUBJECT AND ANGINA PECTORIS PATIENT

COMPARISON OF hPGDS CONCENTRATION BETWEEN CORONARIA BLOOD AND GREAT CARDIAC VEIN BLOOD BEFORE PTCA

COMPARISON OF hPGDS CONCENTRATION IN PERIPHERAL BLOOD
BETWEEN NORMAL SUBJECT AND ANGINA PECTORIS PATIENT

TIME COURSE OF CHANGE IN hPGDS CONCENTRATION
IN GREAT CARDIAC VEIN BLOOD OF ANGINA PECTORIS PATIENT AFTER PTCA

COMPARISON OF hPGDS CONCENTRATION IN CEREBROSPINAL FLUID BETWEEN NORMAL SUBJECT AND CEREBRAL INFARCTION PATIENT

COMPARISON OF hPGDS CONCENTRATION IN PERIPHERAL BLOOD BETWEEN NORMAL SUBJECT AND CEREBRAL INFARCTION PATIENT

METHODS AND KITS FOR DETECTING OR PREDICTING ISCHEMIC DISORDERS

The present application is a national phase application of international application Ser. No. PCT/JP98/01972, filed under 37 C.F.R. §371, which claims benefit of priority of JP 113126/1997. These applications are explicitly incorporated herein by reference in their entirety and for all purposes.

TECHNICAL FIELD

The present invention relates to a method for detecting or predicting ischemic disorders by using as an indication the concentration of human lipocalin-type prostaglandin D synthase (hereinafter, simply referred to as "hPGDS") in body fluid samples.

BACKGROUND ART

Prostaglandin $D_2$ is a physiologically active substance synthesized from arachidonic acid, and can be produced from prostaglandin H with PGD synthase. Recently, it has been found that hPGDS is identical with β-trace that has been known to be found in human cerebrospinal fluid (hereinafter, simply referred to as "CSF") in a large amount and such distribution of hPGDS in a human body suggests some association with neurological disorders. hPGDS has also been known to be found in semen, amniotic fluid and the like, and therefore it has been proposed to utilize hPGDS for the assessment of fertility (i.e., assessment of azoospermia), diagnosis of fetal development, and the like. However, no report suggesting the correlation between hPGDS and ischemic disorders has been found.

Arteriosclerosis, which is a major factor of ischemic disorders, has two types: atherosclerosis arising at relatively large arteriae and aortae; and arteriolosclerosis arising at peripheral arteriolae. Atherosclerosis provokes outgrowth of foam cells, proliferation of fibrae, hyperplasia of tunica intima vasorum, caused by lipid deposits, thrombogenesis, and calcification resulting in stenosis or occlusion of lumens; thus ischemic disorders are produced. Arteriolosclerosis provokes the increase in connective fibrae in tunica intima, resulting in strong hyalinization. Such hyalinization often extends to tunica media. In this case, the arteria are hyalinized and thickened and lumens are narrowed, resulting in ischemic disorders. In general, the cause of arteriosclerosis is considered as follows. When endothelial cells are impaired by any factor such as hyperlipidemia or hypertension, monocytes infiltrate into the walls of the arteriae from the circulating blood together with serum components and were transformed to macrophages. The macrophages incorporate oxidized low density lipoprotein (LDL) that had been undergone oxidization and denaturation in the vessel walls and were transformed to foam cells. The activated endothelial cells, macrophages or adhesive platelets release growth factors or chemotaxis factors, which induces the migration into tunica intima or proliferation of smooth muscle cells. The smooth muscle cells also accumulate lipids therein and consequently are transformed to foam cells. Thereafter, hyperplasia of tunica intima, atheroma formation, stenosis of lumen, ulcer formation and cicatrization are developed. In this manner, arteriosclerosis plaques are formed.

Disorders in which interference with blood flow is induced by coronary sclerosis are called ischemic heart disorders, such as angina pectoris and myocardial infarction. Ischemic heart disorders provoke cerebral circulatory disorders (e.g., cerebral infarction) at cerebral arteriae and obturating arteriosclerotic disorders at peripheral arteriae. Arteriolosclerosis is accompanied by hyperplasia and degeneration of tunica intima and tunica media caused by hyalinization thereof, and it predominantly provoke cerebral and renal disorders.

All types of ischemic disorders progress without any of their characteristic symptoms or signs at the early stage, and none of the clinical symptoms appears until the lesion progresses to an advanced stage. However, up to now, no effective biochemical detection method applicable for the prediction of ischemic disorders during such period of stage has been developed. At the point of time where the symptoms appear and abnormality in the results of clinical trials associated with the development of the symptoms are observed, the lesions do give rise to the terminal phase. At present, there is no screening method that exactly diagnoses the lesions at the early stage, therefore diagnosis of arteriosclerosis is based on the cumulative assessment of risk factors such as lipids in serum, hypertension and smoking.

As mentioned above, there is no reliable method for diagnosis of the lesion at the early stage for ischemic disorders. Moreover, after any clinical symptom appears, patients with ischemic disorders are needed for extremely severe life management and therapy. Therefore, it is an urgent demand to develop a screening method that exactly diagnoses the lesion of an ischemic disorder at its early stage.

DISCLOSURE OF THE INVENTION

Prostaglandin $D_2$ exhibits supressive action against organic change associated with arteriosclerosis, such as an inhibiting coagulation. Therefore, the present inventors have focused on the correlation between prostaglandin $D_2$ synthesizing enzyme, hPGDS, and arteriosclerosis. For the purpose of overcoming the above-mentioned problems, the present inventors determined the hPGDS concentrations in body fluid samples (e.g., blood, cerebrospinal fluid, urine) from normal subjects, and established reference value for each type of body fluid sample. Based on the reference value, it was examined whether the hPGDS concentration in a body fluid sample from a test subject was suitable as the indication of the early stage of an ischemic disorder, in other words, whether the hPGDS concentration in a body fluid sample has any correlation with the ischemic disorder. As a result, it was found that the hPGDS concentration in fluid samples collected from a patient with ischemic disorder or body fluid sample from the patient collected before he was diagnosed as such showed significant difference from the reference values, hPGDS concentrations established from normal subjects. This finding leads the possibility of prediction or detection of an ischemic disorder in a patient at the early stage by monitoring the kinetics of hPGDS in a body fluid sample. It is also found that the method of the present invention can exactly predict an ischemic disorder at its earlier stage, prior to the prediction method based on the cumulative assessment of risk factors (e.g., hypertension, lipids in serum, smoking).

Accordingly, the present invention provides a method for detecting or predicting ischemic disorders comprising determining the concentration of hPGDS in a body fluid sample. The body fluid sample includes blood, urine, cerebrospinal fluid, saliva or semen. The method for the determination of the hPGDS concentration includes an immunological assay. In the present invention, it is preferable that the detection or prediction of an ischemic disorder be made by the comparison between the hPGDS concentration in a body fluid sample from a test subject and those from a normal subject.

The ischemic disorder to be detected or predicted includes those resulted from arteriosclerosis or embolus; ischemic heart disorders (e.g., myocardial infarction, angina pectoris); cerebral infarction; intracranial hemorrhages (e.g., intracerebral hemorrhage, subarachnoid hemorrhage, subdural hemorrhage); aneurysms (e.g., dissecting aneurysm, abdominal aortic aneurysm); nephrosclerosis; myocardial infarction developed as a sequela of Kawasaki disease; and the like.

The present invention also provides a kit for detecting an ischemic disorder which comprises an antibody specific to hPGDS. Preferably, the kit comprises first and second antibodies specific to hPGDS. In this case, the second antibody is preferably capable of binding to a conjugate of hPGDS with the first antibody. Both the first and second antibodies are preferably monoclonal antibodies. An example of the first antibody is a monoclonal antibody 7F5 (described below), and an example of the second antibody is a monoclonal antibody 1B7 (described below).

BEST MODE FOR CARRYING OUT THE INVENTION

Figure 1:
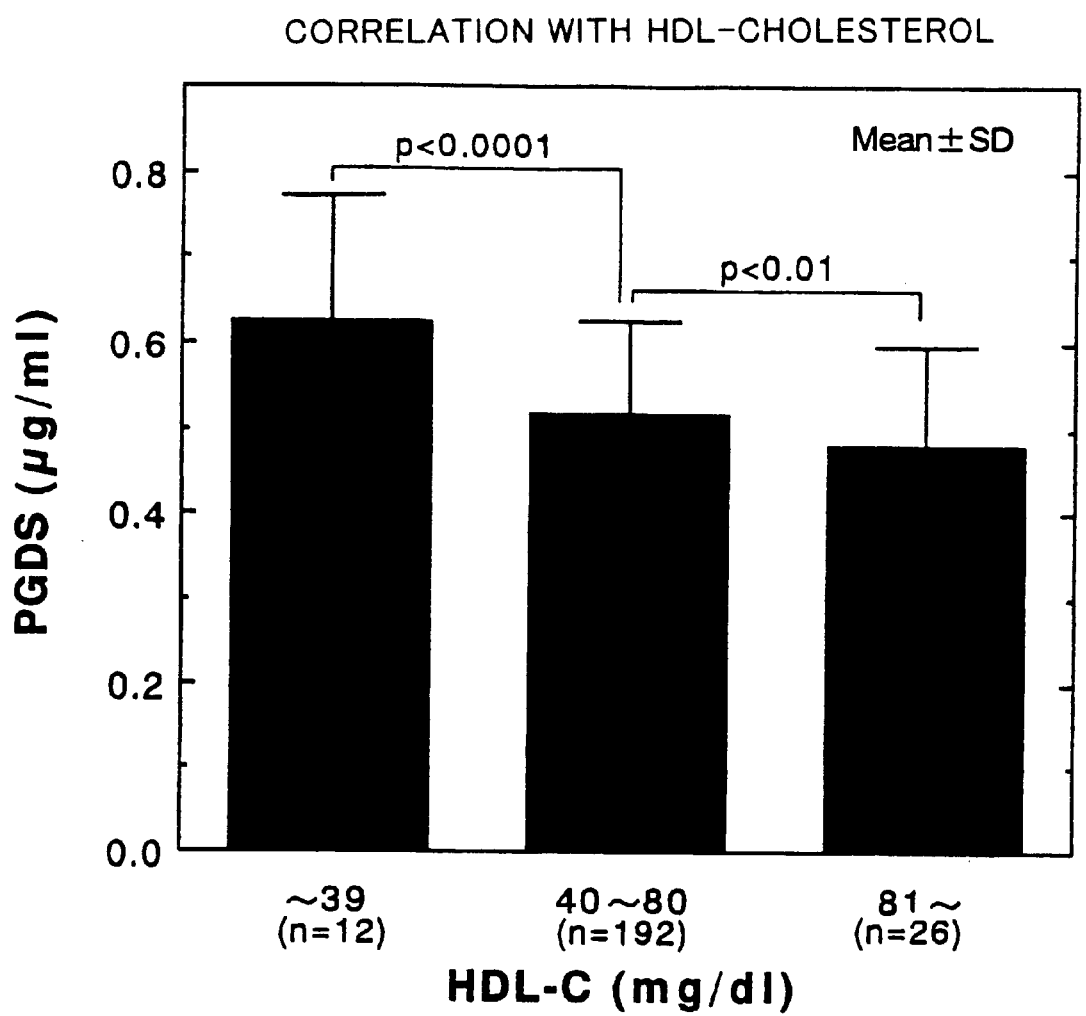
FIG. 1 is a graph illustrating the correlation between the PGDS (µg/ml) concentration and the HDL-C (mg/dl) concentration in peripheral blood.

Hereinbelow, the present invention will be described in detail.

The correlation between the hPGDS concentration in a body fluid sample from a patient with an ischemic disorder and a normal subject was examined. As a result, it was observed that the hPGDS concentration in a body fluid sample from a patient with an ischemic disorder is likely to vary compared with that from a normal subject. Accordingly, by collecting a body fluid sample from a subject and determining the hPGDS concentration in the sample, it becomes possible to detect or predict whether the subject would develop an ischemic disorder or not.

In a preferable embodiment according to the present invention, two antibodies sandwich ELISA may be employed for the detection of hPGDS. The two antibodies used in the two antibodies sandwich ELISA are preferably anti-hPGDS monoclonal antibodies each recognizing different epitopes. One (i.e., a first antibody) of these two antibodies may be coated onto any carrier (e.g., a microtiter plate) to immobilize hPGDS thereon. The other (i.e., a second antibody) may be any one as long as it can bind to the immobilized hPGDS. The second antibody is preferably labeled with a detectable substance for the subsequent detection step. An example of the detectable labeling substance is biotin. The detection of biotin may be conducted by any known method, and preferably by the method in which a conjugate of streptavidin with a peroxidase is bound to the biotin. The peroxidase includes horseradish peroxidase. For the detection of the peroxidase, it is preferable to use a substrate capable of developing a color by the action of the peroxidase.

Both the two antibodies can be produced appropriately by persons skilled in the art and are not particularly limited. Preferably, the two antibodies may be a monoclonal antibody 1B7 produced from cell line 1B7 and a monoclonal antibody 7F5 produced from cell line 7F5, respectively.

These cell lines have been deposited at the National Institute of Bioscience and Human-technology, Agency of Industrial Science and Technology, Japan (1–3, Higashi 1-chome, Tsukuba-shi, Ibaraki-ken, Japan) under the accession No. FERM BP-5709 for 1B7 (deposition date: Sep. 21, 1995) and the accession No. FERM BP-5711 for 7F5 (deposition date: Jun. 6, 1996). The method for producing the monoclonal antibodies from the corresponding cell lines may be any one known to those skilled in the art. When these two antibodies are used, it is preferable to use 7F5 as the first antibody and 1B7 as the second antibody.

For the detection of hPGDS using the above-mentioned substances, first, hPGDS may be bound to the first antibody that has been immobilized onto a carrier (e.g., a microtiter plate). Next, the biotin-labeled second antibody may be bound to the immobilized hPGDS, and then a conjugate of streptavidin-horseradish peroxidase is bound to the biotin moiety of the second antibody. Finally, a substrate capable of developing a color by the action of horseradish peroxidase is added to the reaction mixture to cause the color development, and then the developed color is quantified. When TM-Blue (INTERGEN) is used as the color-developing substance, the developed color can be quantified by adding a 0.5 N sulfuric acid solution as a terminating solution to the reaction solution, stirring the resultant reaction solution, and then measuring the absorbance at 450 nm of the reaction solution using a plate reader or the like.

The value obtained is compared with the reference value established for normal subjects. Since the reference value varies depending on the types of the body fluid sample, it is necessary to previously establish the reference value for the type of the body fluid sample to be tested. The reference value may be established based on the values given by the determination of the hPGDS concentrations in individual body fluid samples from several normal subjects. In this case, the determination of the hPGDS concentration may also be conducted by any one of the above-mentioned methods. The establishment of the reference value from the determined values can be conducted appropriately by those skilled in the art. Preferably, the reference value is defined as "mean value± standard deviation" of the determined values. The comparison of the hPGDS concentration in a body fluid sample from a subject with the reference value established as described above may be conducted by any method known to those skilled in the art, and preferably by the comparison with a criterion value determined based on the reference value. In this case, when the value determined for a subject is higher than the criterion value, the subject is judged to have a high probability of already having or being at a risk of having the ischemic disorder. The criterion value is preferably defined as [the mean value+2×(the standard deviation)].

According to the present invention, the detection and the prognostic management of ischemic disorders (e.g., myocardial infarction, angina pectoris, cerebral infarction, intracerebral hemorrhage, subarachnoid hemorrhage, subdural hemorrhage, dissecting aneurysm, abdominal aortic aneurysm, nephrosclerosis) in subjects, as well as the prediction of subjects at a high risk of having such ischemic disorders, are possible. The detection of ischemic disorders in subjects or the prediction of subjects at a high risk of having ischemic disorders may be conducted by the method as mentioned above. The prognostic management may be conducted by monitoring the hPGDS concentration in a fluid sample from a patient with an ischemic disorder after the patient is subjected to a therapeutic treatment.

Further, the present invention provides a kit for detecting an ischemic disorder, which is applicable for the practice of the method of the present invention. The kit comprises an antibody specific to hPGDS, whereby the detection of the ischemic disorder can be carried out using the antibody in an immunological assay. When two antibodies sandwich ELISA is employed as the immunological assay, the kit may comprise first and second antibodies specific to hPGDS. The second antibody is preferably capable of binding to a conjugate of hPGDS and the first antibody. For this purpose, for example, an antibody that recognizes an epitope different from that recognized by the first antibody may be used as the second antibody. It is preferable that the first and second antibodies be monoclonal. antibodies. Such first antibody includes a monoclonal antibody 7F5, and such second antibody includes a monoclonal antibody 1B7.

The kit of the present invention may further comprise a substance and/or a device suitable for the detection of antibodies, the immobilization of antibodies, and the like. To immobilize the antibody, the kit may further comprise a carrier (e.g., a microtiter plate), a solution for the immobilization (e.g., carbonate buffer) and a blocking solution (e.g., gelatin-containing PBS). For the detection of the antibodies, it is preferable that the antibodies be labeled previously. In this case, the kit may further comprise a detecting reagent for detecting the label. For example, when biotin is used as the labeling substance, the detecting reagent may comprise a conjugate of streptavidin with horseradish peroxidase (HRP) as well as a color-developing solution that is capable of developing a color by the action of HRP.

Hereinbelow, the present invention will be described in more detail with reference to the following Examples. However, it should be understood that the invention is not limited to the specific details set forth in the Examples.

EXAMPLE 1

Determination of the hPGDS Concentrations in Peripheral Blood, Great Cardiac Vein Blood and Cerebrospinal Fluid, and Establishment of the Reference Values for the Individual Types of Fluid Samples The entitled body fluid samples were collected from normal subjects, the concentrations of hPGDS in the peripheral blood, the great cardiac vein blood and the cerebrospinal fluid were determined. Based on the determined values, the reference values were established for the individual types of fluid samples. In this procedure, the peripheral blood, the great cardiac vein blood and the cerebrospinal fluid were collected from 12 subjects, 6 subjects and 8 subjects, respectively, and then determined on the hPGDS concentrations as follows. The hPGDS concentration in each sample was conducted by two antibodies sandwich ELISA. That is, first, an anti-hPGDS monoclonal antibody (clone: 7F5) capable of binding to hPGDS was dissolved in a 50 mM carbonate buffer (pH 9.6) at a concentration of 4.4 $\mu$g/ml, added to each well of a 96-well microtiter plate at a volume of 300 $\mu$l/well. The plate was allowed to stand at 4° C. overnight, thereby immobilizing the antibody onto the surface of the wells. The plate was washed with phosphate-buffered saline (PBS; pH 7.4) three times, added with PBS containing 0.2% gelatin (a blocking solution; pH 7.4) at a volume of 300 $\mu$l/well, and incubated at 30° C. for 90 minutes. A series of the standard solutions were prepared by stepwise dilution of hPGDS purified from the cerebrospinal fluid (hereinafter, simply referred to as "CSF") with the blocking solution, and used to construct the standard curve for hPGDS. The above-prepared post-blocking plate was washed with PBS containing 0.05% Tween 20 (T-PBS) three times. Each well of the plate was added with 100 $\mu$l of each of the standard solutions or a solution of the sample appropriately diluted with the blocking solution, and then the plate was incubated at 30° C. for 90 minutes. The plate in which the antigen was reacted with the antibody was washed with T-PBS three times. Each well of the plate was added with 100 $\mu$l of a solution of biotin-labeled anti-hPGDS monoclonal antibody (clone: 1B7) diluted with the blocking solution, and then the plate was incubated at 30° C. for 90 minutes. The biotin-labeled anti-hPGDS monoclonal antibody used in this procedure was one capable of binding to hPGDS and prepared by biotinylating an anti-hPGDS monoclonal antibody 1B7 that recognized an epitope different from that recognized by the immobilized monoclonal antibody 7F5. After washing the plate, each well of the plate was added with 100 $\mu$l of a solution of a streptavidin-HRP (horseradish peroxidase) conjugate (Biosouce, Cat.#: 6467) diluted with the blocking solution. The plate was incubated at 30° C. for 90 minutes. After washing the plate with T-PBS three times, each well of the plate was added with 100 $\mu$l of a color-developing solution (TM-Blue: INTERGEN). After incubating the plate at 30° C. for 20 minutes, 100 $\mu$l of a terminating solution (0.5 N sulfuric acid) was added to each well of the plate and stirred using a plate mixer to terminate the reaction. The absorbance at 450 nm of the solution in each well was measured using a commercial plate reader (Seikagaku Corporation; Cat.#. Sk601).

Both the hybridomas that produced the monoclonal antibodies 1B7 and 7F5 used in the above procedure, respectively, were prepared by cell fusion of the antibody-producing cells generated from animals immunized with hPGDS and myeloma cells as described in WO 97/16461.

The monoclonal antibody-producing cell lines were designated corresponding to the names of the monoclonal antibodies, respectively, and have been deposited at the National Institute of Bioscience and Human-technology, Agency of Industrial Science and Technology, Japan (1–3, Higashi 1-chome, Tsukuba-shi, Ibaraki-ken, Japan) under the accession No. FERM BP-5709 for 1B7 (deposition date: Sep. 21, 1995) and the accession No. FERM BP-5711 for 7F5 (deposition date: Jun. 6, 1996). The production of the monoclonal antibodies was conducted in the following manner. Mice were injected with PRISTANE intraperitoneally at a dose of 1.0 ml/mouse. After 2 weeks, the mice were implanted intraperitoneally with either the above-mentioned cell line 1B7 or 7F5 at $1\times10^8$ cells/mouse. After additional 2 weeks, the ascites was removed from each mouse. The ascites was fractionated by chromatography on a Protein A affinity column to give each of the monoclonal antibodies at a concentration of 3–10 mg/ml.

As a result, it was found that the reference values given from the samples from normal subjects were 0.373±0.024 μg/ml for the peripheral blood, 0.424±0.034 μg/ml for the great cardiac vein blood, and 11.61±3.08 μg/ml for the cerebrospinal fluid (mean value j standard deviation; ditto for the data shown below).

EXAMPLE 2
Correlation Between the hPGDS Concentration in Peripheral Blood and Various hemobiochemical Items in Normal Subjects The determination of the hPGDS concentration was conducted using peripheral blood collected from normal subjects. The peripheral blood was collected from 230 subjects and used to determine the hPGDS concentration in blood in the same manner as in Example 1. The concentrations of total cholesterol (T-CHO), high density lipoprotein (HDL), low density lipoprotein (LDL), triglyceride (TG) and uric acid were also determined by the conventional methods.

As a result, it was found that, in the peripheral blood, there was a negative correlation between the HDL concentration, one of risk factors of arteriosclerosis, and the hPGDS concentration (FIG. 1). However, no correlation was observed between the concentrations of the substances other than HDL and the hPGDS concentration.

EXAMPLE 3
Immunohistochemical Staining

The distribution of hPGDS in cardiac tissues was examined by immunohistochemical staining using anti-hPGDS monoclonal antibodies.

The procedure for the preparation of specimens was as follows. A specimen was fixed with a 4% paraformaldehyde solution (containing a 10% sucrose solution; pH 7.5) for 3–4 hours at 4° C. The resultant specimen was allowed to stand at 4° C. for 5 to 24 hours in an above solution supplemented with acetic acid (about 5%) so as to adjust the pH to 3.5–4.0. The resultant specimen was sectioned into pieces of 6–10 μm thickness in accordance with the conventional paraffin section preparation method. The sections were deparaffinized in a conventional manner. Thereafter, the section was subjected to a two-step procedure prior to the subsequent blocking treatment. That is, first, the plate was immersed in a methanol solution containing 0.3% hydrogen peroxide at room temperature for 30 minutes, and then immersed in 0.3% pepsin/0.01N acetic acid solution at room temperature for 5 minutes. Subsequently, the section was subjected to blocking with 10% normal sheep serum/Tris buffered saline/ 0.05% Triton X100 at room temperature for 1 hour. The section was subjected to the reaction with the primary antibody and subsequently with the biotinylated secondary antibody. The color development was conducted with 3', 3'-diaminobenzidine and hydrogen peroxide using Histofine PAP kit (Nichirei Corporation). The nuclear staining was conducted in a 1% cresyl violet/30% ethanol solution. After dehydration, the section was mounted with xylene, and then subjected to observation.

Figure 2:
FIG. 2 is an image of immunohistochemically stained tunica intima of the left atrium.
Figure 3:
FIG. 3 is an image of immunohistochemically stained lesion of the early stage arteriosclerosis at the coronaria.
Figure 4:
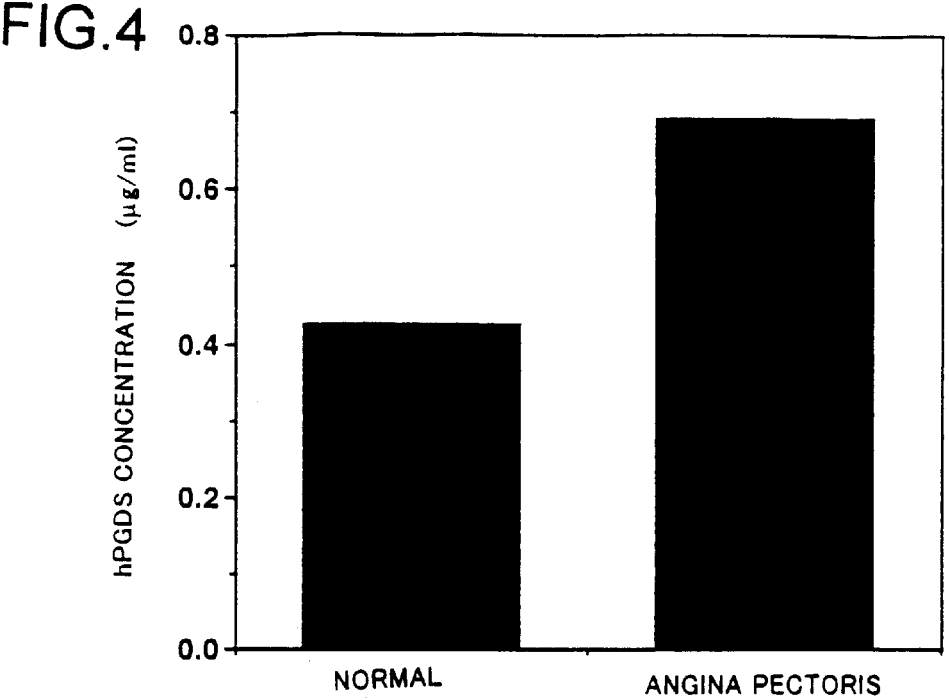
FIG. 4 is a graph for the comparison of the hPGDS concentration in great cardiac vein blood between normal subjects and patients with angina pectoris.
Figure 5:
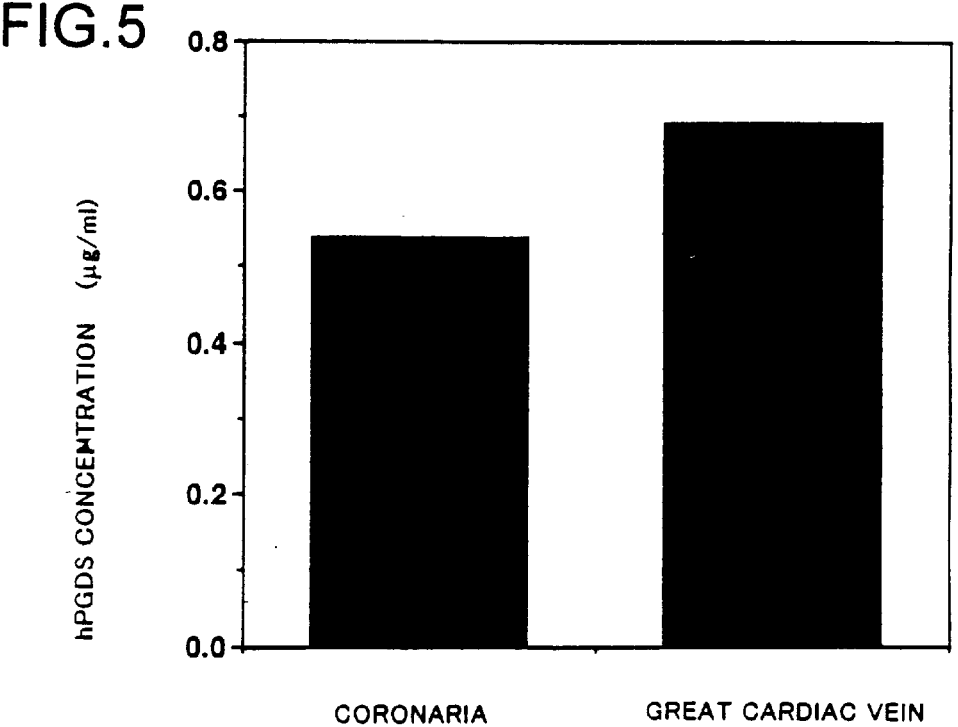
FIG. 5 is a graph for the comparison of the hPGDS concentration between coronaria blood and great cardiac vein blood before the practice of PTCA.
Figure 6:
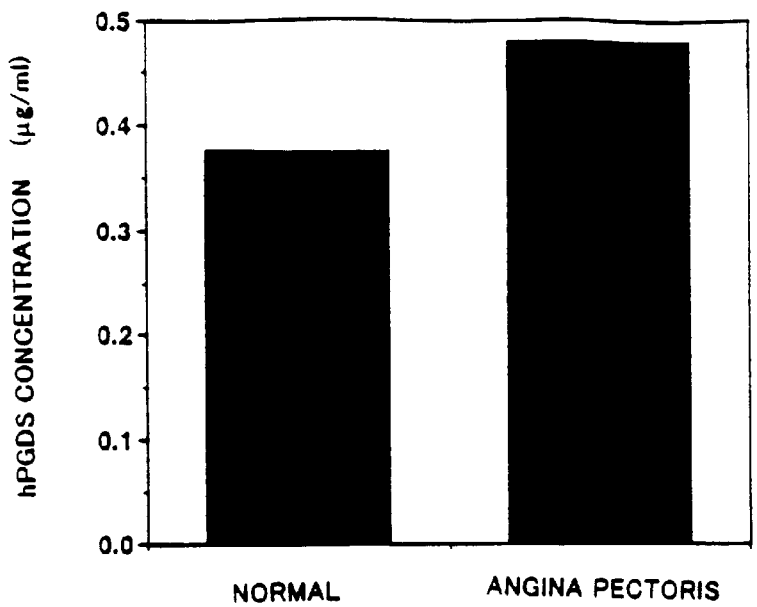
FIG. 6 is a graph for the comparison of the hPGDS concentration in peripheral blood between normal subjects and patients with angina pectoris.
Figure 7:
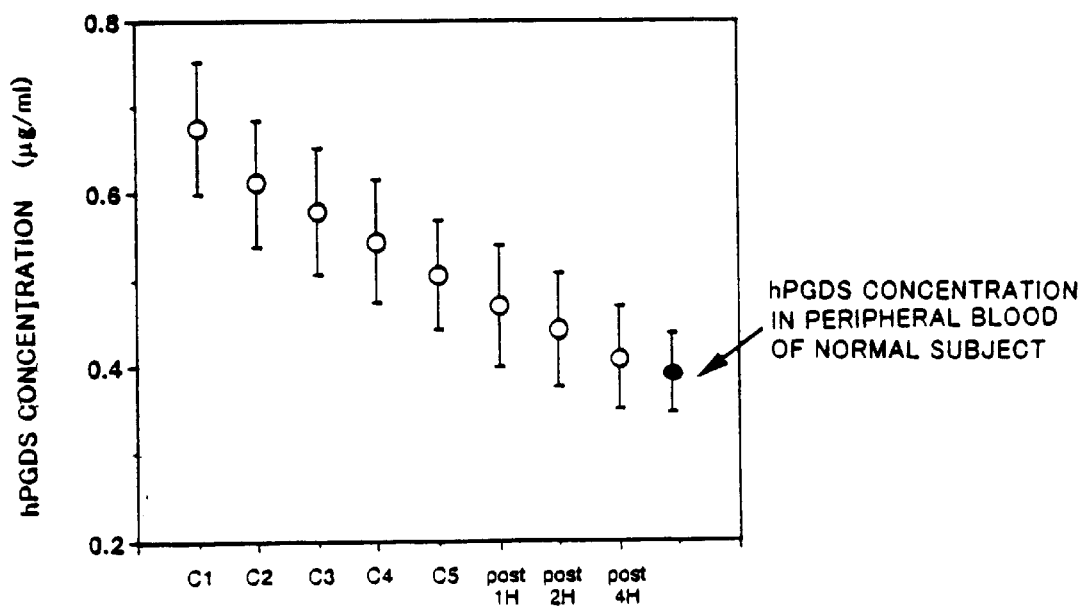
FIG. 7 is a graph showing the time course of the change in the hPGDS concentration in great cardiac vein of patients with angina pectoris after the practice of PTCA.

As shown in FIG. 2, the immunoreactivity for hPGDS was observed in the endocardial cells of the left atrium. Morphologically, these cells were considered to be endothelial cells. The immunoreactivity for hPGDS was also found in a part of the endothelial cells in the coronary artery. These results clearly demonstrate that hPGDS is produced in endothelial cells. In addition, as shown in FIG. 3, hPGDS-positive cells were found in the peripheray of the early stage atherosclerosis lesion in the tunica intima of the coronary artery (colony of smooth muscle cells in the synthetic state).

These results clearly demonstrate that hPGDS has a close relation with the early stage lesion of arteriosclerosis.

EXAMPLE 4
Examination of the Correlation Between Angina Pectoris and the hPGDS Concentration in Blood To examine the correlation between angina pectoris associated with arteriosclerosis and the hPGDS concentration, blood was collected from a patient with angina pectoris prior to the percutaneous transluminal coronary angioplasty (hereinafter, simply referred to as "PTCA").

The peripheral blood and the great cardiac vein blood were collected from 5 patients with angina pectoris prior to the PTCA. In addition, blood was collected from the great cardiac vein of the patients after PTCA. These blood samples were centrifuged for use as the test samples. The determination of the serum hPGDS concentrations was conducted in the same manner as in Example 1.

The results are shown in FIGS. 4, 5, 6 and 7. As a result, it was found that the hPGDS concentration in the great cardiac vein of patients with angina pectoris was 0.691±0.109 μg/ml, which was significantly higher than that of normal subjects (0.424±0.017 μg/ml); and that before PTCA, the hPGDS concentration in the great cardiac vein (0.691±0.109 μg/ml) is significantly higher than that in the coronary artery (0.537±0.144 μg/ml). These results demonstrate that the amount of hPGDS is up-regulated in response to the arteriosclerosis development at the coronary arterial vessels.

The hPGDS concentration in the peripheral blood of patients with angina pectoris (0.480±0.098 μg/ml) was also significantly different from that of normal subjects (0.373±0.024 μg/ml), demonstrating that the up-regulation occurring at the cardiac blood vessel is reflected in a peripheral level. These results clearly show that it is possible to detect angina pectoris by the comparison of the hPGDS concentration in the peripheral blood of a test subject with that of a normal subject.

After PTCA, the hPGDS concentration in the great cardiac vein blood was decreased with the elapse of time, and reached to almost the same level as a normal subject at the recovery stage. These results showed that the method of the present invention enables the prognostic management of angina pectoris patients after PTCA.

EXAMPLE 5
Comparison of the Lipid Concentration and the hPGDS Concentration in Blood in Patients with Angina Pectoris For three patients with angina pectoris who were considered to have advanced arteriosclerosis based on echo of internal carotid artery, difference in blood pressure between the upper limb and the lower limb, stress electrocardiography, ability to platelet aggregation and funduscopy, and for three normal subjects, the lipid and the hPGDS concentration in peripheral blood were determined, and examined the correlation between these concentrations and arteriosclerosis. With respect to the lipid in blood, high density lipoprotein (hereinafter, referred to as "HDL") and low density lipoprotein (hereinafter, referred to as "LDL"), both which are established as risk factors of arteriosclerosis, were measured in a conventional manner. In general, risk of arteriosclerosis is judged as "high" when the HDL concentration is low and the LDL concentration is high. Therefore, in this example, 40 mg/dl or lower for the HDL concentration and 150 mg/dl or higher for the LDL concentration were judged as "high risk". The determination of the hPGDS concentration in blood was conducted in the same manner as in Example 1, and the reference value of the hPGDS concentration was established to be 0.373±0.048 [mean value+2×(standard deviation)] μg/ml, the concentration above this value was judged as "high risk" of arteriosclerosis. The results are shown in Table 1 below.

TABLE 1

Comparison between lipid concentration and hPGDS concentration in blood as the diagnostic data for angina pectoris

|  | hPGDS (μg/ml) | HDL (mg/dl) | LDL (mg/dl) |
| --- | --- | --- | --- |
| Normal subject 1 | 0.40 | 42 | 112 |
| Normal subject 2 | 0.35 | 61 | 105 |
| Normal subject 3 | 0.33 | 50 | 145 |
| Patient with angina pectoris 1 | 1.10* | 29* | 201* |
| Patient with angina pectoris 2 | 0.93* | 43 | 120 |
| Patient with angina pectoris 3 | 0.78* | 49 | 222* |
| Criterion | 0.426 or higher | 40 or lower | 150 or higher |

The values from which risk of angina pectoris is predicted are marked with *.

In all of the three normal subjects tested, the serum hPGDS concentration fell within the reference value. In contrast, in the patients with angina pectoris tested, the serum hPGDS concentration was higher than the reference value in all of the patients, the serum HDL concentration was lower than the reference value (40 mg/dl) in one out of three of the patients, and the serum LDL concentration was higher than the reference value (150 mg/dl) in two out of three of the patients (one of the two patients was not the same patient as the patient showing the lower HDL concentration). These results show that the hPGDS concentration detects the arteriosclerotic lesion better than both the HDL concentration and the LDL concentration that are established risk factors, and therefore effective for the prediction of arteriosclerosis.

EXAMPLE 6
Examination of the Correlation Between Cerebral Infarction and the hPGDS Concentration in CSF The correlation between cerebral infarction associated with arteriosclerosis and the serum hPGDS concentration was examined by collecting CSF from patients with cerebral infarction and determining the amount of hPGDS therein.

Figure 8:
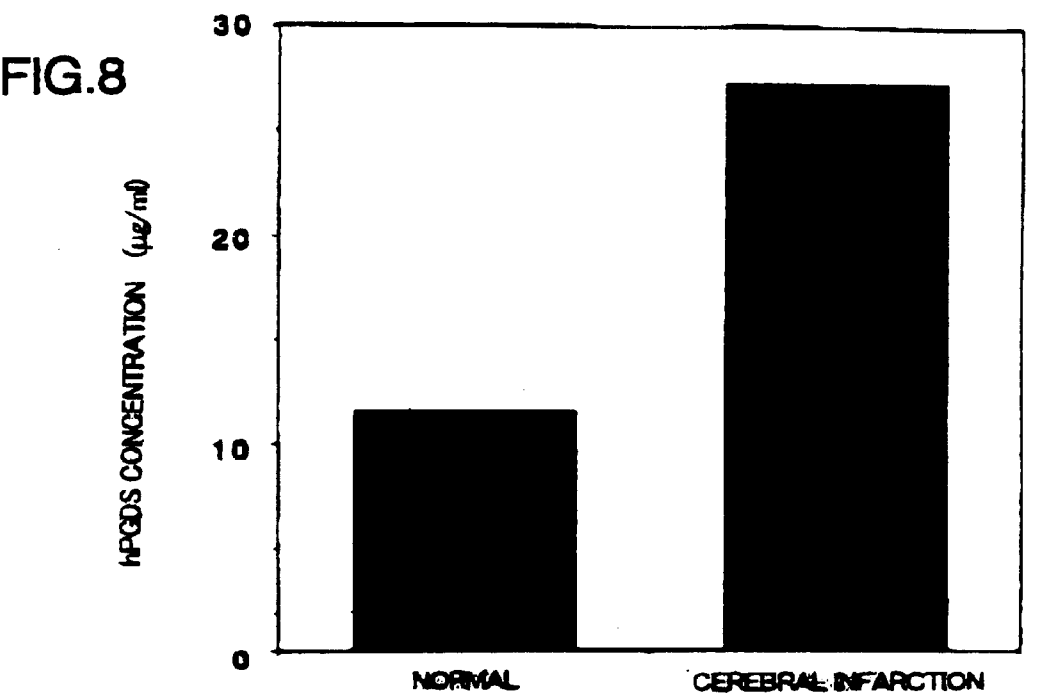
FIG. 8 is a graph for the comparison of the hPGDS concentration in cerebrospinal fluid between normal subjects and patients with cerebral infarction.

The CSF was collected from five patients with cerebral infarction, and the hPGDS concentration therein was determined in the same manner as in Example 1. The results are shown in FIG. 8. As a result, it was found that the hPGDS concentration in CSF of the patients with cerebral infarction was 27.308±3.52 μg/ml, which was significantly different from that of normal subjects. These results clearly demonstrate that cerebral infarction can be detected by the comparison of the hPGDS concentration in CSF of the subject with that of a normal subject.

EXAMPLE 7
Examination of the Correlation Between Cerebral Infarction and the hPGDS Concentration in Blood The correlation between cerebral infarction associated with arteriosclerosis and the serum hPGDS concentration was examined by collecting peripheral blood from patients with cerebral infarction and determining the amount of hPGDS therein.

Figure 9:
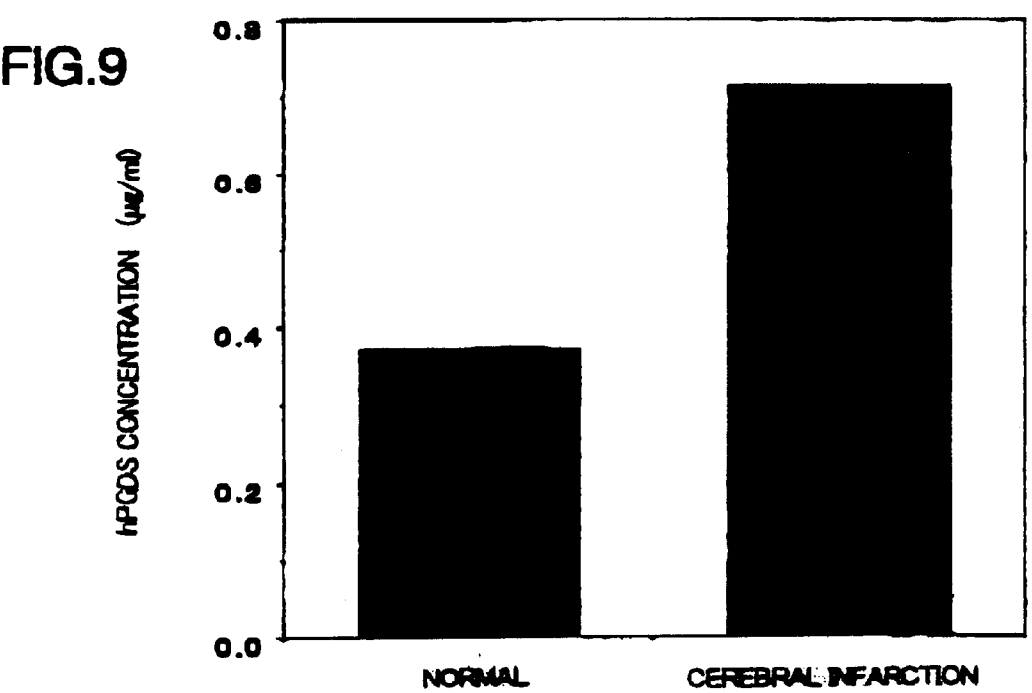
FIG. 9 is a graph for the comparison of the hPGDS concentration in peripheral blood between normal subjects and patients with cerebral infarction.

The peripheral blood was collected from five patients with cerebral infarction, and the hPGDS concentration therein was determined in the same manner as in Example 1. The results are shown in FIG. 9. As a result, it was found that the hPGDS concentration in peripheral blood of the patients with cerebral infarction was 0.716±0.258 μg/ml, which was significantly different from that of normal subjects (0.373±0.024 μg/ml). These results clearly demonstrate that the cerebral infarction in a subject can be detected by the comparison of the hPGDS concentration in peripheral blood of the subject with that of a normal subject.

EXAMPLE 8
Prediction of Ischemic Disorders

To make clear the correlation between the early stage lesion of arteriosclerosis and the serum hPGDS concentration, or to compare with the prior method based on cumulative assessment of established risk factors, blood samples that had been collected from seven patients with an ischemic disorder associated with arteriosclerosis before the patients were diagnosed as the ischemic disorder and had been stored before use, were used to determine the serum hPGDS concentration. The comparison was made between the positivity predicted by the method of the present invention and that predicted by the prior method. In the cumulative assessment, risk of arteriosclerosis in a subject was assessed comprehensively based on the following seven factors, T-CHO, HDL, LDL, TG, blood sugar, uric acid and smoking which were determined in a conventional manner, in which the criteria of these factors were 220 mg/dl or higher, 40 mg/dl or lower, 150 mg/dl or higher, 150 mg/dl or higher, 140 mg/dl or higher, 7.5 mg/dl or higher, and 20 cigarettes per day for a time of period of 10 years or longer, respectively, as the criteria. In the method of the present invention, the serum was measured in the same manner as in Example 1, and the serum hPGDS concentration of 0.373+ 0.048 [mean value+2×(standard deviation)] μg/ml or higher was used as the criterion of the assessment. The results are shown in Tables 2 and 3 below.

TABLE 2

Prediction of ischemic disorder based on the hPGDS concentration in blood

|  | Subject 1 | Subject 2 | Subject 3 | Subject 4 | Subject 5 | Subject 6 | Subject 7 |
| --- | --- | --- | --- | --- | --- | --- | --- |
| hPGDS concentration (μg/ml) | 1.13* | 0.72* | 0.56* | 0.98* | 1.31* | 0.40 | 0.69* |
| Judgement | + | + | + | + | + | − | + |

Criterion: 0.426 μg/ml or higher.
The values higher than the criterion are marked with*.

TABLE 3

Prediction of ischemic disorder by cumulative assessment
based on T-CHO, HDL, LDL, TG, blood sugar, uric acid and smoking

|  | subject 1 | Subject 2 | Subject 3 | Subject 4 | Subject 5 | Subject 6 | Subject 7 |
|---|---|---|---|---|---|---|---|
| T-CHO | 200 | 275* | 190 | 263* | 287* | 220* | 253* |
| HDL | 51 | 29* | 58 | 24* | 43 | 59 | 35* |
| LDL | 123 | 222* | 150* | 205* | 211* | 120 | — |
| TG | 142 | 157* | 40 | 162* | 155* | 56 | 82 |
| Blood sugar | 100 | 94 | 88 | 111 | 184* | 126 | 96 |
| Uric acid | 5 | 5.5 | 6.2 | 7.8* | 6.1 | 6.3 | 6.0 |
| smoking | Yes* | Yes* | Yes* | No | No | Yes* | No |
| Judgement | − | + | − | + | + | − | + |

Criteria:
T-CHO: 220 or higher,
HDL: 40 or lower,
LDL: 150 or higher,
TG: 150 or higher,
blood sugar: 140 or higher,
uric acid: 7.5 or higher,
and smoking: yes.
The data higher (lower, as for HDL) than the individual criteria are marked with*.

As shown in Tables 2 and 3, according to the prior method, four out of seven of the subjects tested were judged as being at high risk of the ischemic disorder. In contrast, according to the method of the present invention, six out of seven of the subjects tested were predicted as being at high risk of an ischemic disorder. These results demonstrate that the method of the present invention enables to predict the development of an ischemic disorder in a subject at a higher odds ratio than the prior method.

Industrial Applicability

By utilizing the method of the present invention, the detection and prediction of ischemic disorders can be conducted conveniently at a high odds ratio.

What is claimed is:

1. A method for detecting or predicting an ischemic disorder in a subject, the method comprising the following steps:
   (a) providing a first and a second body fluid sample, wherein the first sample is taken from a test subject from which an ischemic disorder is to be detected or predicted and the second sample is taken from a normal subject, and the body fluid sample is selected from the group consisting of a blood sample, a urine sample, a saliva sample and a semen sample;
   (b) providing a first antibody and a second labeled antibody, wherein both the first and the second antibodies are capable of specifically binding to a human lipocalin-type prostaglandin D synthase, and a detecting reagent capable of detecting the label;
   (c) contacting the first antibody, the second labeled antibody, and the detecting reagent with the first body fluid sample;
   (d) contacting the first antibody, the second labeled antibody, and the detecting reagent with the second body fluid sample; and,
   (e) detecting the amount of and determining the concentration of human lipocalin-type prostaglandin D synthase in the normal subject sample to provide a reference value and detecting the amount of and determining the concentration of human lipocalin-type prostaglandin D synthase in the test subject sample, wherein an increased concentration of human lipocalin-type prostaglandin D synthase in the test subject sample compared to the reference value indicates that the test subject has a high probability of having had or being at risk of having an ischemic disorder.

2. A method for detecting or predicting an ischemic disorder in a subject, the method comprising the following steps:
   (a) providing a body fluid sample from a normal subject, wherein the body fluid sample is selected from the group consisting of a blood sample, a urine sample, a saliva sample and a semen sample,
   (b) providing a first antibody and a second labeled antibody, wherein both the first and the second antibodies are capable of specifically binding to a human lipocalin-type prostaglandin D synthase, and a detecting reagent capable of detecting the label;
   (c) providing a reference value of the concentration of human lipocalin-type prostaglandin D synthase in the normal body fluid sample provided in step (a) using the first antibody, the second labeled antibody, and the detecting reagent;
   (d) providing a test body fluid sample from a test subject from which an ischemic disorder is to be detected or predicted, wherein the body fluid is the same type of body fluid provided in (a);
   (e) contacting the first antibody, the second labeled antibody, and the detecting reagent with the test subject body fluid sample;
   (f) detecting the amount of and determining the concentration of human lipocalin-type prostaglandin D synthase in the normal subject sample to generate a reference value, wherein an increased concentration of human lipocalin-type prostaglandin D synthase in the test subject sample compared to the reference value indicates that the test subject has a high probability of having had or being at risk of having an ischemic disorder.

3. The method of claim 1 or 2, wherein the concentration of lipocalin-type prostaglandin D synthase in the body fluid sample from the subject is determined by an immunological assay.

4. The method of claim 1 or 2, wherein the body fluid sample is blood.

5. The method of claim 1 or 2, wherein the ischemic disorder is caused by arteriosclerosis.

6. The method of claim 1 or 2, wherein the ischemic disorder is caused by an embolus.

7. The method of claim 1 or 2, wherein the ischemic disorder is an ischemic heart disorder.

8. The method of claim 7, wherein the ischemic heart disorder is a myocardial infarction or an angina pectoris.

9. The method of claim 1 or 2, wherein the ischemic disorder is a cerebral infarction.

10. The method of claim 1 or 2, wherein the ischemic disorder is an intracranial hemorrhage.

11. The method of claim 10, wherein the intracranial hemorrhage is selected from the group consisting of an intracerebral hemorrhage, a subarachnoid hemorrhage and a subdural hemorrhage.

12. The method of claim 1 or 2, wherein the ischemic disorder is an aneurysm.

13. The method of claim 12, wherein the aneurysm is a dissecting aneurysm or an abdominal aortic aneurysm.

14. The method of claim 1 or 2, wherein the ischemic disorder is a nephrosclerosis.

15. The method of claim 1 or 2, wherein the ischemic disorder is a myocardial infarction developed as a sequela of Kawasaki disease.

16. The method of claim 1 or 2, wherein to indicate that the test subject has a high probability of having or being at risk of having an ischemic disorder, the amount of lipocalin-type prostaglandin D synthase in the test subject sample is greater than a reference value defined as a mean value plus twice the standard deviation of the lipocalin-type prostaglandin D synthase concentrations in the normal subject samples.

17. The method of claim 1 or 2, wherein the lipocalin-type prostaglandin D synthase in the body fluid sample is a human lipocalin-type prostaglandin D synthase.

18. The method of claim 1 or 2, wherein in step (b) the method provides an immobilized first antibody.

19. A kit for detecting an ischemic disorder comprising two antibodies, a detecting reagent, and instructions, wherein each antibody has specific reactivity for a human lipocalin-type prostaglandin D synthase and the instructions set forth a method comprising the following steps:

(a) providing a first and a second body fluid sample, wherein the first sample is taken from a test subject from which an ischemic disorder is to be detected or predicted and the second sample is taken from a normal subject, and the body fluid sample is selected from the group consisting of a blood sample, a urine sample, a saliva sample and a semen sample;

(b) providing a first antibody and a second labeled antibody, wherein both the first and the second antibodies are capable of specifically binding to a human lipocalin-type prostaglandin D synthase, and a detecting reagent capable of detecting the label;

(c) contacting the first antibody, the second labeled antibody, and the detecting reagent with the first body fluid sample;

(d) contacting the first antibody, the second labeled antibody, and the detecting reagent with the second body fluid sample; and, (e) detecting the amount of and determining the concentration of human lipocalin-type prostaglandin D synthase in the normal subject sample to provide a reference value and detecting the amount of and determining the concentration of human lipocalin-type prostaglandin D synthase in the test subject sample, wherein an increased concentration of human lipocalin-type prostaglandin D synthase in the test subject sample compared to the reference value indicates that the test subject has a high probability of having had or being at risk of having an ischemic disorder.

20. A kit for detecting an ischemic disorder comprising two antibodies, a detecting reagent, and instructions, wherein each antibody has specific reactivity for a human lipocalin-type prostaglandin D synthase and the instructions set forth a method comprising the following steps:

(a) providing a body fluid sample from a normal subject, wherein the body fluid sample is selected from the group consisting of a blood sample, a urine sample, a saliva sample and a semen sample, (b) providing a first antibody and a second labeled antibody, wherein both the first and the second antibodies are capable of specifically binding to a human lipocalin-type prostaglandin D synthase, and a detecting reagent capable of detecting the label;

(c) providing a reference value of the concentration of human lipocalin-type prostaglandin D synthase in the normal body fluid sample provided in step (a) using the first antibody, the second labeled antibody, and the detecting reagent;

(d) providing a test body fluid sample from a test subject from which an ischemic disorder is to be detected or predicted, wherein the body fluid is the same type of body fluid provided in (a);

(e) contacting the first antibody, the second labeled antibody, and the detecting reagent with the test subject body fluid sample;

(f) detecting the amount of and determining the concentration of human lipocalin-type prostaglandin D synthase in the normal subject sample to generate a reference value, wherein an increased concentration of human lipocalin-type prostaglandin D synthase in the test subject sample compared to the reference value indicates that the test subject has a high probability of having had or being at risk of having an ischemic disorder.

21. The kit of claim 19 or claim 20, further comprising a second antibody capable of binding to a lipocalin-type prostaglandin D synthase immobilized by the first antibody.

22. The kit of claim 21, wherein the second antibody is labeled with a detectable substance.

23. The kit of claim 22, wherein the detectable substance comprises biotin.

24. The kit of claim 23, further comprising a conjugate of streptavidin.

25. The kit of claim 19 or claim 20, wherein the antibody is a monoclonal antibody.

26. The kit of claim 25, wherein the monoclonal antibody is monoclonal antibody accession no. 1B7, FERM BP-5709.

27. The kit of claim 25, wherein the monoclonal antibody is monoclonal antibody accession no. 7F5, FERM BP-5711.

28. A method for detecting or predicting an ischemic disorder in a subject, the method comprising the following steps:

(a) providing a first and a second body fluid sample, wherein the first sample is taken from a test subject from which an ischemic disorder is to be detected or predicted and the second sample is taken from a normal subject, and the body fluid sample is selected from the group consisting of a blood sample, a urine sample, a saliva sample and a semen sample;

(b) providing a first antibody and a second labeled antibody, wherein both the first and the second antibodies are capable of specifically binding to a human lipocalin-type prostaglandin D synthase, and a detecting reagent capable of detecting the label;

(c) contacting the first antibody, the second labeled antibody, and the detecting reagent with the first body fluid sample;

(d) contacting the first antibody, the second labeled antibody, and the detecting reagent with the second body fluid sample; and, (e) detecting the amount of and determining the concentration of human lipocalin-type prostaglandin D synthase in the normal subject sample to provide a reference value and detecting the amount of and determining the concentration of human lipocalin-type prostaglandin D synthase in the test subject sample, wherein an increased concentration of human lipocalin-type prostaglandin D synthase in the test subject sample compared to the reference value indicates that the test subject has a high probability of having had or being at risk of having an ischemic disorder, wherein the ischemic disorder is caused by a member of the group consisting of an arteriosclerosis, an embolus, an ischemic heart disorder, a myocardial infarction, an angina pectoris, an aneurysm, a dissecting aneurysm, an abdominal aortic aneurysm, a nephrosclerosis, and a myocardial infarction developed as a sequelae of Kawasaki disease.

29. A method for detecting or predicting an ischemic disorder in a subject, the method comprising the following steps:

(a) providing a body fluid sample from a normal subject, wherein the body fluid sample is selected from the group consisting of a blood sample, a urine sample, a saliva sample and a semen sample, (b) providing a first antibody and a second labeled antibody, wherein both the first and the second antibodies are capable of specifically binding to a human lipocalin-type prostaglandin D synthase, and a detecting reagent capable of detecting the label;

(c) providing a reference value of the concentration of human lipocalin-type prostaglandin D synthase in the normal body fluid sample provided in step (a) using the first antibody, the second labeled antibody, and the detecting reagent;

(d) providing a test body fluid sample from a test subject from which an ischemic disorder is to be detected or predicted, wherein the body fluid is the same type of body fluid provided in (a);

(e) contacting the first antibody, the second labeled antibody, and the detecting reagent with the test subject body fluid sample;

(f) detecting the amount of and determining the concentration of human lipocalin-type prostaglandin D synthase in the normal subject sample to generate a reference value, wherein an increased concentration of human lipocalin-type prostaglandin D synthase in the test subject sample compared to the reference value indicates that the test subject has a high probability of having had or being at risk of having an ischemic disorder;

wherein the ischemic disorder is caused by a member of the group consisting of an arteriosclerosis, an embolus, an ischemic heart disorder, a myocardial infarction, an angina pectoris, an aneurysm, a dissecting aneurysm, an abdominal aortic aneurysm, a nephrosclerosis, and a myocardial infarction developed as a sequelae of Kawasaki disease.

30. A method for detecting or predicting an ischemic disorder in a subject comprising a two antibody sandwich immunoassay, the method comprising the following steps:

(a) providing a first and a second body sample in a fluid form, wherein the first sample is taken from a test subject from which an ischemic disorder is to be detected or predicted and the second sample is taken from a normal subject;

(b) providing a first antibody specific to a lipocalin-type prostaglandin D synthase and a second labeled antibody specific to a lipocalin-type prostaglandin D synthase;

(c) contacting the first antibody and the second labeled antibody with the first body sample;

(d) contacting the first antibody and the second labeled antibody with the second body sample; and, (e) detecting the amount of and determining the concentration of lipocalin-type prostaglandin D synthase in the normal subject sample to generate a reference value, and detecting the amount of and determining the concentration of lipocalin-type prostaglandin D synthase in the test subject sample, wherein an increased concentration of lipocalin-type prostaglandin D synthase in the test subject sample compared to the reference value indicates that the test subject has a high probability of having had or being at risk of having an ischemic disorder.

31. The method of claim 30, wherein in step (b) the method provides an immobilized first antibody.

32. The method of claim 31, wherein the first antibody is immobilized on a microtiter plate.

33. The method of claim 30, wherein the immunoassay comprises an enzyme immunoassay or a radioimmunoassay.

34. The method of claim 30, wherein in step (b), the label of the second labeled antibody comprises biotin, and the second antibody is detected by the method further providing an composition conjugated to streptavidin and adding the composition to the contacted first antibody and the second labeled antibody of step (d), wherein the composition is directly detectable or the composition generates a second directly detectable composition.

35. The method of claim 34, wherein the detectable composition is an enzyme.

36. The method of claim 35, wherein the enzyme is a peroxidase.

37. The method of claim 36, wherein the peroxidase is a horseradish peroxidase.

38. The method of claim 35, wherein the enzyme generates a detectable colored composition.

39. The method of claim 30, wherein the first antibody or the second antibody is a monoclonal antibody.

40. The method of claim 30, wherein the first antibody or the second antibody is a polyclonal antibody.

41. The method of claim 30, wherein the first antibody is a monoclonal antibody and the second antibody is a polyclonal antibody.

* * * * *

UNITED STATES PATENT AND TRADEMARK OFFICE
CERTIFICATE OF CORRECTION

PATENT NO.      : 6,461,827 B1                                          Page 1 of 1
DATED           : October 8, 2002
INVENTOR(S)     : Hiroshi Oda et al.

It is certified that error appears in the above-identified patent and that said Letters Patent is hereby corrected as shown below:

<u>Title page,</u>
Item [73], Assignee, please correct the spelling of the assignee to:

-- Maruha Corporation, Tokyo, Japan --

Signed and Sealed this

Eighth Day of July, 2003

JAMES E. ROGAN
*Director of the United States Patent and Trademark Office*